United States Patent [19]

Gardineer et al.

[11] 4,282,755

[45] Aug. 11, 1981

[54] TRANSDUCER DRIVE AND CONTROL

[75] Inventors: Bayard G. Gardineer, Skillman; George W. Leber, Delran, both of N.J.

[73] Assignee: Technicare Corporation, Solon, Ohio

[21] Appl. No.: 100,598

[22] Filed: Dec. 5, 1979

[51] Int. Cl.³ ............................................. G01N 29/04
[52] U.S. Cl. ..................................................... 73/634
[58] Field of Search ......................... 73/618, 633, 634; 128/660

[56] References Cited

U.S. PATENT DOCUMENTS 4,177,679  12/1979  Soldner .................... 73/633

Primary Examiner—Anthony V. Ciarlante
Attorney, Agent, or Firm—Audley A. Ciamporcero, Jr.

[57] ABSTRACT

In an ultrasound imaging system employing a moving or oscillating transducer, actual transducer position is detected periodically, rather than continuously. A magnet is caused to oscillate with the transducer, and periodic alignment of the magnet with a fixedly mounted Hall effect switch provides synchronization data for sonic pulse generation, pulse-echo receipt, and image assembly and display.

8 Claims, 5 Drawing Figures

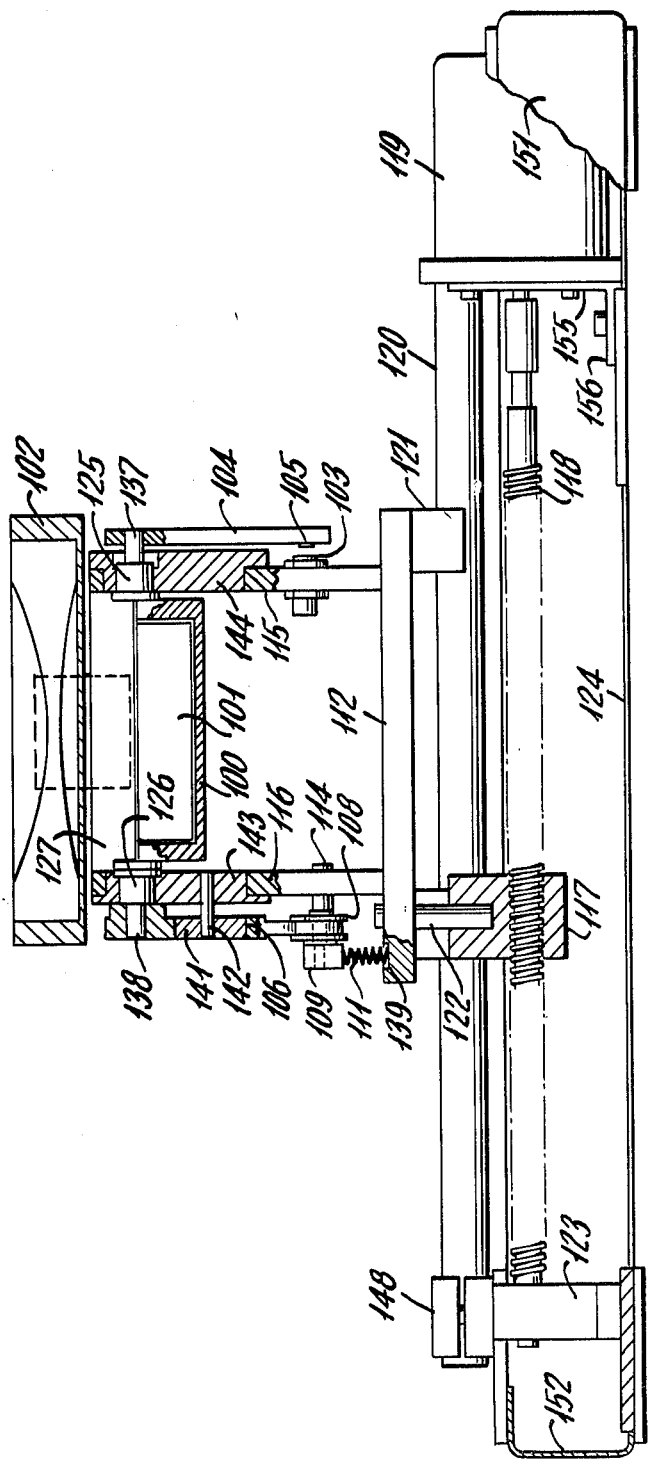

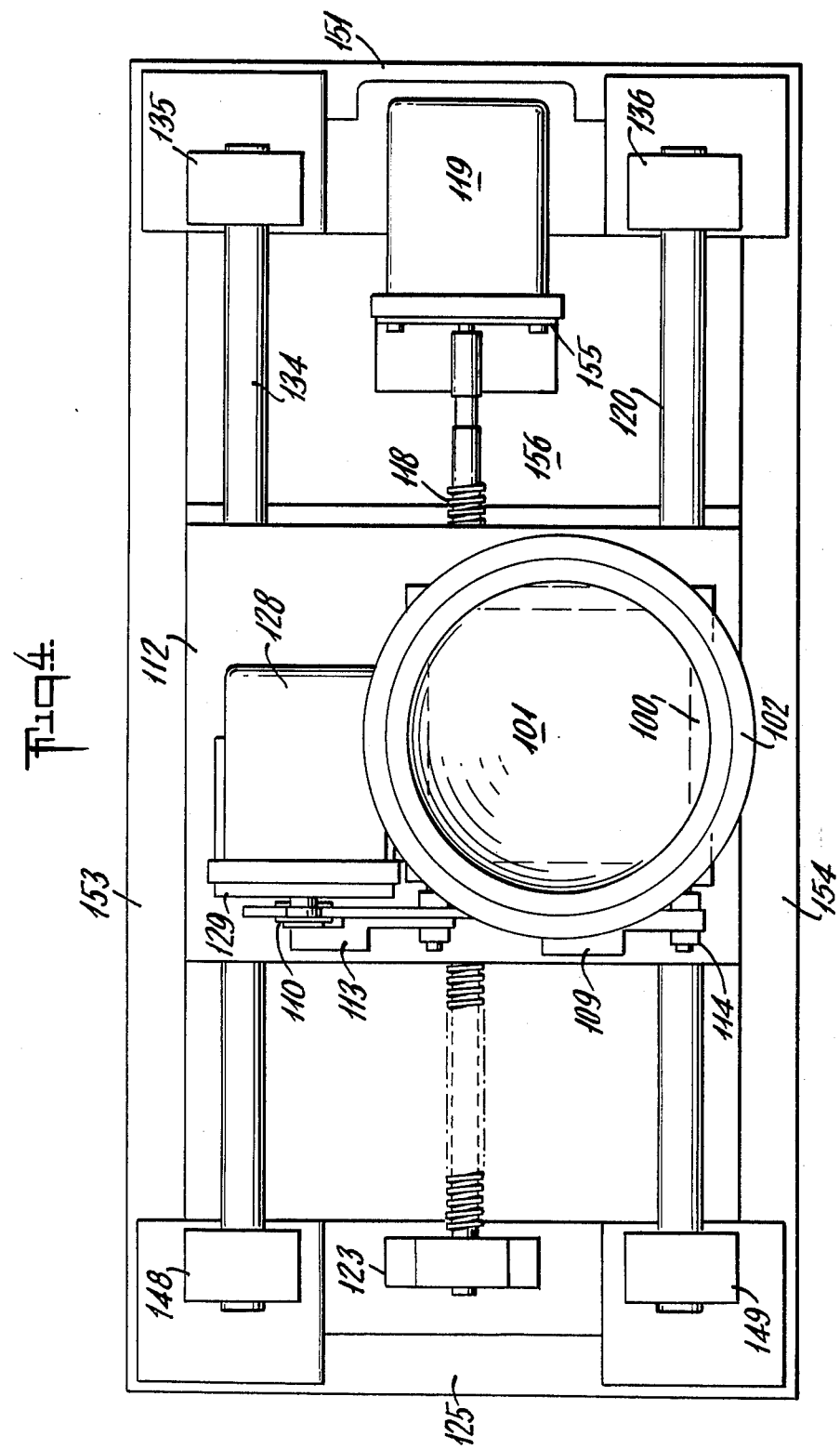

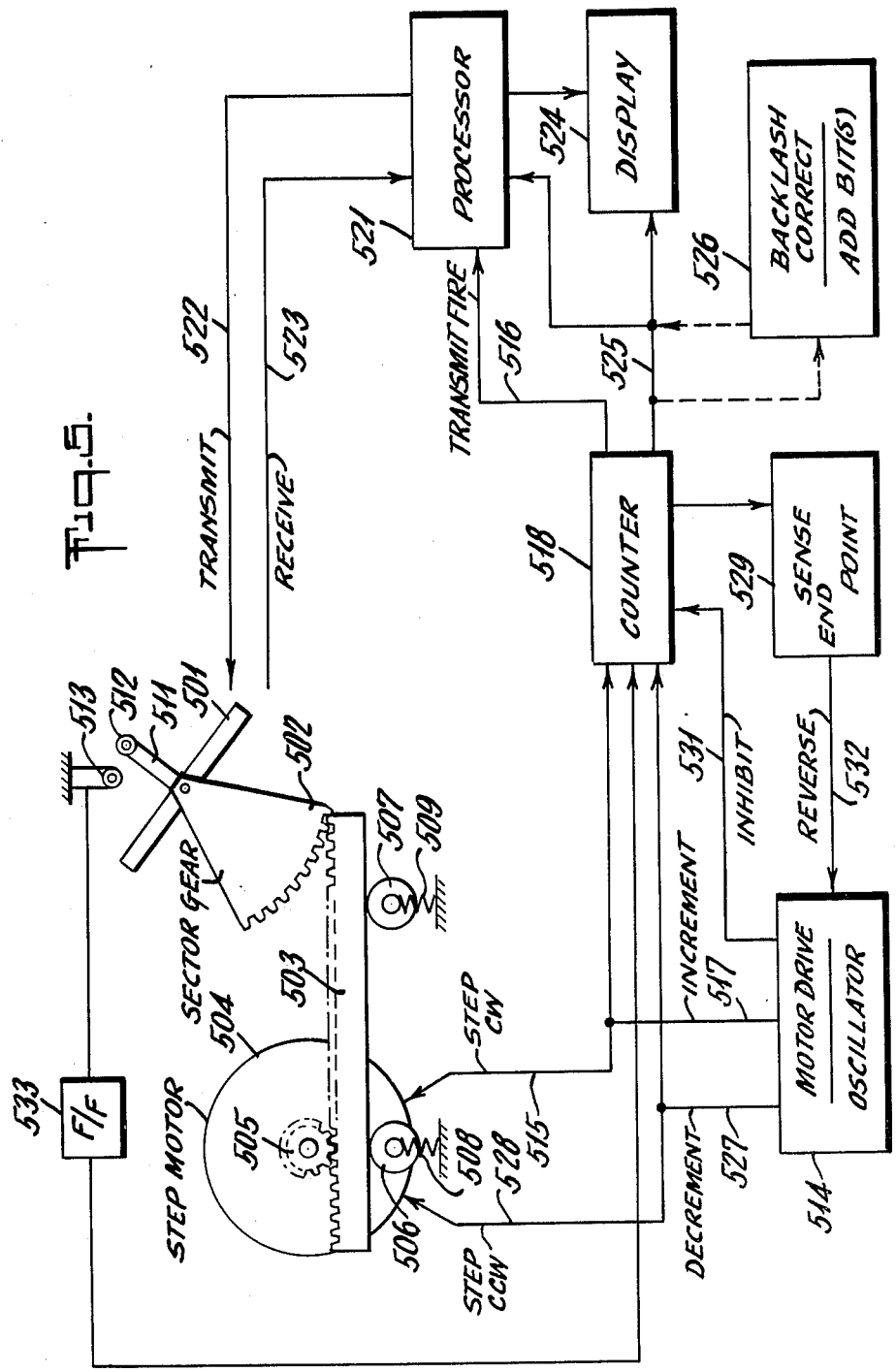

TRANSDUCER DRIVE AND CONTROL

FIELD OF THE INVENTION

This invention relates to ultrasound diagnostic imaging systems, and more particularly to methods and apparatus for controlling and monitoring motion of transducers in specified subclasses of such systems.

BACKGROUND OF THE INVENTION AND PRIOR ART

Ultrasound imaging systems have become a well-accepted and important modality of diagnosis and guidance in many health care fields. For example, fetal monitoring, abdominal soft tissue study, and cardiac monitoring have all incorporated ultrasound systems as an essential aspect of effective diagnosis and treatment. Real time systems, wherein organ and organism motion and development is observed as it occurs, has allowed practitioners to review many physiological conditions in vivo, in substitution for traumatic exploratory surgery, or, worse still, for essential uncertainty as to the nature of a patient's condition.

In accordance with the knowledge of those of ordinary skill in the art, real time scanning systems work in a number of ways, including scanning an area of tissue by physical movement of an ultrasound transducer. In some systems, the transducer is coupled directly to the body of the patient, whereas in others the transducer is spatially separated from the body of the patient by a sonically conductive water path. In either case, as the transducer is "wobbled," typically by a stepping motor, the transducer is alternatively conditioned to transmit a pulse of sonic energy into a tissue region, and then to receive echoes resulting from passage of the pulse through various tissue interfaces. Electronic signal processing and display apparatus assembles information resulting from the echoes, and based on the transducer position and focal conditions, and upon the relative timing of the pulse transmission and echo receipts, a representation or image of the irradiated tissue is assembled. For real time systems, which require a high frame repetition rate, it is vital that pulse transmission and echo receipt be carefully timed and coordinated with respect to the transducer positioning, and further that all such transmission and reception information be well coordinated with the sequential rotational displacement of the transducer itself.

Recently, moving transducers have been applied to other sorts of ultrasound diagnostic systems, including water path systems useful for screening specific organs, such as the breast, for malignancies. In accordance with such systems, the patient is conveniently positioned with the breast downwardly suspended in a tank of water, and from beneath, an oscillating or "nodding" transducer is scanned across the breast area, yielding a succession of spaced apart "B" scan images. In the aggregate, these scans depict substantially all tissue within the breast, subject only to the limits of resolution of the system with respect to each scan, and the spacings of the separate scans. While such screening systems may or may not be utilized by the practitioner as real time systems, the continuous, serial accumulation of data, in a rapid fashion to assemble a significant number of frames of information in a short time, imposes similar timing and signal processing constraints as are in effect in real time imaging of moving organs or organisms. Clearly, failure accurately to correlate transmit data with received data, and in turn with transducer positioning, will completely obviate the effectiveness of scanning for small (e.g. 1-3 millimeters) lesions, either by improperly locating them, or by losing the critical data altogether.

One prior art approach to locating accurately the position of an oscillating transducer has been utilization of a rotational variable displacement transformer (RVDT), mounted to the sonic transducer shaft, at all times, to determine the angular position of the transducer and in turn of the transmitted beam. Modulated carrier signals generated by the RVDT typically are digitized by an analog to digital converter, with the digital signal being used to signify angular position of the transducer during an electronic construction of a B-scan image from A-scans taken at discrete transducer positions. Under optimum mechanical and environmental conditions, the RVDT approach yields adequate transducer monitoring and control capacity, but unfortunately such systems have proven to be susceptible to mechanical and environmental difficulties, requiring frequent and difficult maintenance checks and electronic or mechanical corrections.

It is a primary object of the present invention to provide methods and apparatus for accurately monitoring the position of an oscillating, transmitting and receiving sonic transducer in ultra-sound imaging and diagnostic systems. It is an associated object to provide for such monitoring in a fashion which adequately insures the generation of monitoring and control data whereby electronic image reconstruction apparatus functions accurately and rapidly. It is a further object to provide oscillating transducer monitoring and control apparatus and methods which are mechanically and electrically simple and reliable, involving a relative minimum of sensitivity to unavoidable environmental or mechanical wear constraints.

SUMMARY OF THE PRESENT INVENTION

The principles of the present invention involve only intermittent or periodic measurement or observation of transducer position, with predicted or assumed transducer position being utilized during the interleaved periods of time. Hence, rather than employing a continuous monitoring of transducer position, a transducer position signal is generated in accordance with the principles of the present invention only when the transducer passes one or more given reference points, with subsequent data being assembled into an image based upon signals which are provided, since the most recent generation of the reference, to change transducer position.

In a preferred embodiment of the present invention, a sonic transducer is oscillated about a given axis by a stepping motor via a spring loaded rack and gear linkage. The transducer has extended therefrom a rigidly connected but conveniently small magnet, which traverses an arc comparable to the arc of the transducer. A Hall effect switch is located at a convenient point (e.g. at a nominal midpoint) of the magnet arc of traversal, such that the switch is potentially energized by each coincidence of the magnet and the switch. An electronic counter maintains a count of the energizing pulses which have been coupled to the stepping motor, and in turn of the successive positions of the transducer (and magnet). The count in the counter, which is utilized to control image assembly at the scan converter and associated display electronics, is reset at successive or alternate alignments of the magnet and the Hall effect switch.

In such fashion, the maintenance of a count in the counter effectively represents a prediction or assumption as to the position of the transducer, based on signals provided to the motor since the magnet most recently passed the Hall effect switch.

DESCRIPTION OF THE DRAWINGS

FIGS. 1-4 show respective front, back, side, and top views of an immersible, water path ultrasound transducer mechanism which embodies the principles of the invention; and FIG. 5 shows in schematic form a mechanical/electronic system employing the principles of the present invention for assembly and generation of ultrasound images.

BEST MODE FOR CARRYING OUT THE INVENTION

Figure 1:
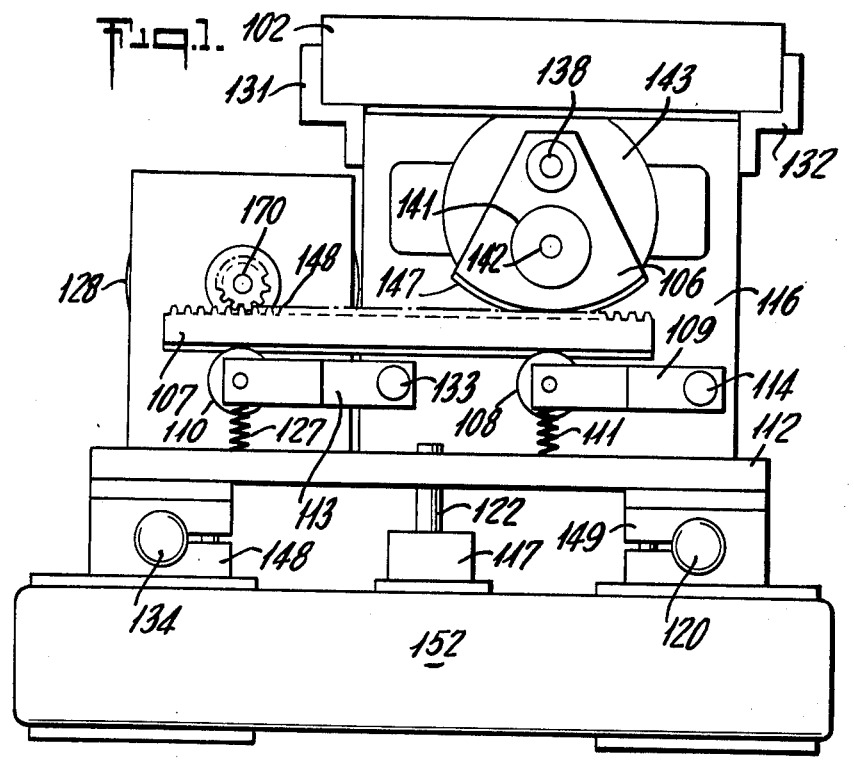

Referring generally to FIGS. 1-4, there is shown an ultrasound scanning apparatus which employs the principles of the present invention. In particular, the apparatus set forth in various views in FIGS. 1-4 constitutes a mechanism adapted to be immersed in a tank of water, into which the breasts of a patient are serially immersed above the scanning mechanism. For each breast, a series of B- scan "slices" are taken, serially across the breast, thereby yielding a comparable series of images which may be reviewed appropriately to identify lesions or suspicious tissue conditions within the breast.

The apparatus shown in FIGS. 1-4 is of the general class described in U.S. Pat. No. 4,131,021 of Mezrich et al. entitled "HIGH RESOLUTION PULSE ECHO ULTRASONIC IMAGING DISPLAY SYSTEM," and in a series of related companion patents to Mezrich et al. Generally, the Mezrich et al. series described pulse echo ultrasound systems which employ a sonic lens intermediate the transducer and the patient.

In such systems, the lens itself has a fixed aperture, typically by positionally fixing the lens, and the scanning of the ultrasound beam through a plane of tissue in interest occurs by manipulation of the beam on the side of the lens opposite the patient. In the embodiment of FIGS. 1-4, the lens itself is immersed in the water path, and the scanning takes place by means of physical oscillation of the transducer through a predetermined arc, typically in the range of thirty degrees. Inasmuch as the focal region of convergence of the lens has a finite depth, each transmission (and reception) of ultrasound pulses at a given position of the transducer yields an A-scan of the tissue within that focal region of convergence. Each half-cycle of oscillation of the transducer, then, results in a collection of A-scan data, which is processed as is known in the art into a complete B-scan picture. In accordance with the embodiment of FIGS. 1-4, an entire carriage or mechanism bearing both the lens and the oscillating or "nodding" transducer is moved transversely below the tissue in interest (i.e. the breast suspended in water above the lens), to assemble a collection of B-scan "slices" which in the aggregate define the full three dimensions of the breast.

Referring with greater particularity to FIGS. 1-4, a base defined by members 151, 152, 153, and 154 lies fixed within a tank of water beneath the location of the breast to be imaged. A motor 119, preferably a stepping motor energized by electrical pulses provided via cable 145, is fixedly carried on the base by means of plates 155 and 156, to drive a threaded shaft 118, which at its other extreme is carried on a bearing 123. A pair of parallel support rails 120 and 34 extend along the length of the support base, rail 120 being rigidly mounted at its extremes on support blocks 149 and 136, and rail 134 being rigidly mounted at its extremes on support blocks 148 and 135. A carriage which bears the sonic transducer and lens assembly rides on rails 120 and 134, and is moved along those rails by engagement of block 117 with the threaded shaft 118. In turn, Block 117 is rigidly connected to the carriage by means of a vertical connecting rod 122.

The carriage defining the ultrasound scanning assembly, which in its entirety is translated along rails 120 and 134 under the power of stepping motor 119, is principally defined by a base member 112 and vertical support side walls 115 and 116. Further, yet another stepping motor 128 is affixed to base member 112 by virtue of vertical mounting plate 129, whereby the stepping motor 128 is integral with the ultrasound scanning carriage, and is moved back and forth on rails 120 and 134 in conjunction therewith. The stepping motor 128, which is energized by signals furnished at cable 146, provides the reciprocal or oscillating motivation for a nodding ultrasound transducer 101, and thereby for generation of each B-scan frame through a collection of respective A-scan pulse-echo combinations emitted from the transducer 101. A sonic lens 102 is rigidly mounted to upright side walls 115 and 116 by transverse brackets 131 and 132. The transducer 101 itself is carried by a bracket 100, which by shaft members 137 and 138 and bearings 125 and 126, pivotably engages plate mountings 143 and 144. In turn, the plate mountings 143 and 144 are respectively attached to the side walls 115 and 116, thereby to mount the transducer 101 pivotably below lens 102, the pivoting occurring on the axis of shafts 137 and 138.

Figure 2:
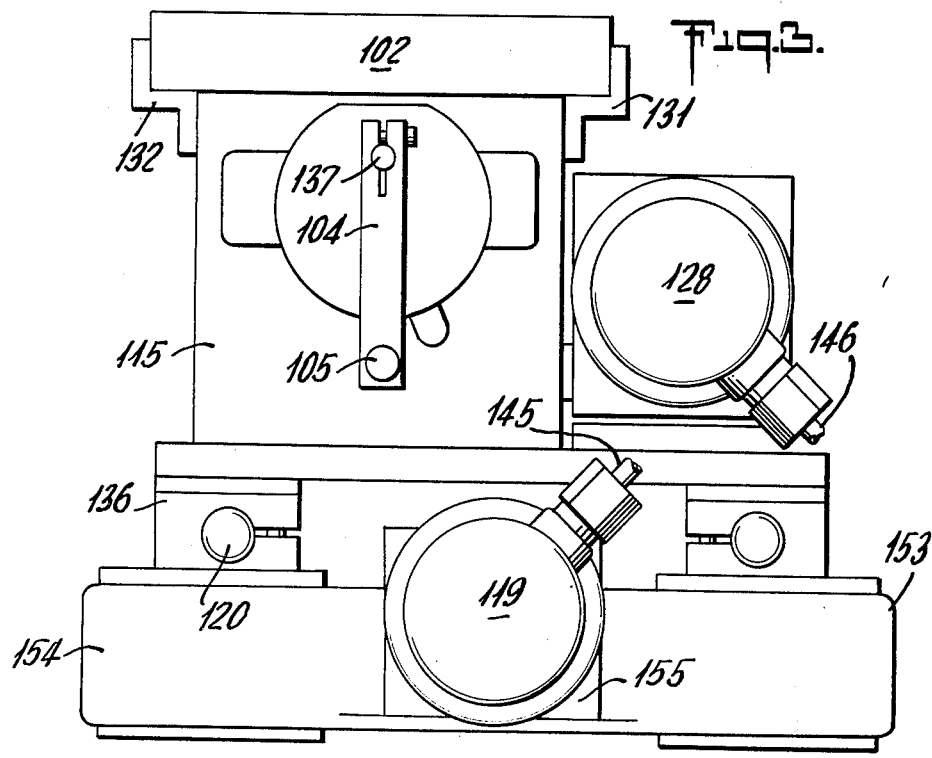

The pivoting transducer 101 may be seen from FIGS. 1, 2 and 4 to be interconnected with the stepping motor 128 by means of a drive gear 170, a rack 107, and a gear sector 106 which is attached to the shaft 138 of transducer bracket 100. As will be noted, the rack 107 is carried on spring loaded "slippers" or rollers 108 and 110, thereby tightly to engage an upper, toothed surface 148 of the rack 107 against correspondingly toothed and engaging gear 170 and the lower toothed portion 147 of gear sector 106. In particular, roller 110 is carried at one extreme of pivot arm 113, which pivots about bolt 133 and is loaded upwardly by spring 127. Similarly, roller 108 is carried at one extreme of lever arm 109, which is pivoted about bolt 114 and is loaded upwardly by spring 111. As will be noted by the partial cutaway in FIG. 2, spring 111 is held by natural tension in a depression 139 in the base plate 112. Spring 127 is similarly mounted in its own depression in base plate 112 (not shown). In a preferred embodiment, gear 170 and gear sector 106 are metallic in construction, whereas the rack 107 is made of a plastic material. The loading of rollers 110 and 108 beneath the mesh points of the rack 107 with gears 170 and 106 prevents gear backlash.

As may be noted most clearly in FIGS. 2 and 3, shaft 137 of transducer bracket 100 protrudes outwardly from plate 144 in wall 115, and rigidly connected thereto is a downwardly depending arm 104. At the lowr terminus of arm 144 is mounted a magnet 105.

As will be best noted from FIG. 2, a commercially available Hall effect switch 103 penetrates and is rigidly mounted to support member 115 advantageously, at the midpoint of the arc travelled by magnet 105 as it moves in conjunction with oscillation of the transducer 101. Hence, the magnet 105 is aligned with the switch 103 once during each half-cycle of oscillation of the transducer 101. The Hall effect switch 103 is of common commercial pedigree, and operates to produce a pulse each time the field generated by magnet 105 is adjacent to (i.e., aligned with) the outer surface of the switch 103. Through conventional wiring, not shown in FIG. 2 but within the routine capability of those of ordinary skill in the art, the Hall effect switch 103 therefore produces two pulses for each full oscillation cycle of the transducer 101.

In partial summary, the apparatus of FIGS. 1–4 represents an immersible carriage and track assembly wherein the carriage holds an acoustic lens and a nodding transducer, as well as stepping motor and linkage apparatus for oscillating that transducer back and forth through a predetermined arc. An extension arm rocks along with the transducer, whereby a Hall effect switch senses occurrence of passage of a magnet at the end of the arm. The entire carriage is moved, transversely to the direction of oscillation of the tranducer, along a track, thereby to enable irradiation of plural parallel planes in the tissue, and assembly of a corresponding plurality of B-scan images of the tissue under examination.

It will be apparent that numerous alternatives may be utilized in substitution for Hall effect switch 103 and magnet 105 without departing from the spirit or scope of the present invention. For example, an optical transceiver may be located on side wall 115 at the point shown for the Hall effect device 103 and spaced therefrom, and in such instance an interrupter is provided at the point on arm 104 occupied by magnet 105, and which passes through the transceiver to break the optical circuit and thus to generate a control pulse. In such instance, interruption of an optical pulse by the interrupter would indicate alignment of the associated point on the arm with the transceiver. The principles of the present invention relating to periodic measurement or location of transducer position and intermittent prediction or assumption of that position would thereby be well saved. Numerous other mechanical, electromagnetic, and the like schemes may similarly be employed.

It is next appropriate to consider FIG. 5, which sets forth a schematic representation of a diagnostic imaging system employing the principles of the present invention. In FIG. 5, a stepping motor 504 drives a gear 505, first in one direction for a number of steps, and then for another, thereby reciprocally to translate the rack 503 back and forth. A gear sector 502 meshes with the rack 503, and thereby is pivoted back and forth, carrying with it a transducer 501 which is connected in common with the sector gear 502. Affixed to and pivoting with the gear 502 and the transducer 501 is an extension or arm 511, which carries at its terminus a magnet 512. Located on the arc of travel of the magnet 512, advantageously at its midpoint, is a Hall effect switch 513. The rack 503 is carried on rollers 506 and 507, which in turn are upwardly loaded by springs 508 and 509, thereby to mesh tightly with gears 502 and 505, and to avoid gear backlash.

Hence, the motor, rack, gear, transducer, and magnet/Hall effect apparatus of FIG. 5 are seen to be symbolic representations of corresponding apparatus in the embodiment set forth in FIGS. 1–4.

FIG. 5 also shows, in symbolic schematic form, certain elements of an ultrasound imaging system adapted to employ the principles of the present invention. In particular, a processor 521, which is understood to include conventional pulse generation and reception apparatus, signal processing and scan conversion apparatus, and the like, is configured in accordance with the knowledge of those of ordinary skill in the art. Hence, upon receipt of energizing pulses via line 516, electrical signals are coupled from processor 521 via line 522 to energize transducer 501 to transmit ultrasound pulses. Thereupon, as echoes are received by the transducer 501, associated electrical signals are coupled by a receive line 523 to the processor 521, for assembly into an image or other suitable representation of the tissue being investigated. In accordance with conventional procedures, pulses transmitted outwardly from transducer 501 along a given line, and corresponding received echoes, may be utilized to assembly an "A-scan" representation of tissue interfaces along that line of flight. As the transducer 501 pivots and generates "A-scans" along plural adjacent lines, a composite "B-scan" may be assembled. Each aggregate B-scan picture or collection of images may be suitably displayed at 524, such as for example on a cathode ray tube display, on video tape or the like retentive media, or by storage of a series of developed photographic images.

As stated, the principles of the present invention relate to timing and control, whereby transmission signals at line 522, received echo signals at line 523, and true, accurate image assembly and display are properly timed and coordinated based on the position of transducer 501 and therefore upon the tissue segment actually being investigated. In FIG. 5, the stepping motor 504 receives actuation signals at lines 515 and 528, the former line 515 energizing steps in one direction (e.g. clockwise) and the latter line 528 energizing steps in the opposite direction (e.g. counterclockwise). These stepping actuation signals are produced by a motor drive 514 which includes an oscillator for generating the actuating signal pulses, each pulse corresponding to initiation of yet another step by motor 504, in a clockwise or counterclockwise direction depending whether the pulse occurs on line 515 or 528. Conventional logic in motor control 514 accomplishes the pulse steering. A counter 518 maintains in storage a count which is incremented via line 517 once for each stepping pulse coupled by the motor drive 514 to stepping motor 504 in the clockwise direction, and which is decremented via line 527 for each stepping pulse generated by motor drive 514 which is coupled to motor 504 via counterclockwise stepping line 528. Preferably, counter 518 utilizes an 8 bit binary encoded representation of a prevailing count, which is coupled via line 524 both to the processor 521 and to the display 524. Assuming, then, that the prevailing count in counter 518 provides an encoded representation of the prevailing position of transducer 501, the coupling of such count via line 525 to the processor 521 and the display 524 thereupon allows data received from the transducer via line 523 to be appropriately located in an image which is being assembled. Such image assembly in the processor 521 is conventionally done by means of digital scan converters, which are in common use and which are commercially available.

Counter 518 is also connected via line 516 to a pulse transmission energizing input of processor 521, whereby on specified count increments (e.g. each increment, alternate increments, periodic increments, or the like), processor 521 is enabled to couple one or more transmission pulses via line 522 to the transducer 501. In a preferred embodiment, a transmit enabling pulse is conveyed by counter 518 to processor 521 via line 516 for alternate counts in counter 518, rather than for every counting increment.

As shown in FIG. 5, line 519 from Hall effect switch 513 is coupled to a reset terminal of counter 518, whereby the count is reset to an appropriate reference value. Optionally, a flip-flop 533 or the like logic couples only alternate pulses from switch 513 to reset the counter. By virtue of the coupling of the 8 bit encoded representation of this reset value to processor 521 and display 524, each resetting of counter 518 enables processor 521 and display 524 to "know" that in fact the data next received via line 523 corresponds to irradiation of a line of tissue at the midpoint of the tissue plane being imaged. During the times when the magnet 512 is not aligned with the Hall effect switch 513, the successive accumulated counts in counter 518, as encoded and coupled to processor 521 and display 524, represent a prediction or assumption as to the corresponding prevailing position of transducer 501, and therefore a corresponding prediction or assumption as to the portion of tissue then being irradiated by a transmitted pulse.

As provided hereinbefore, in a preferred embodiment the gears 505 and 502 are of rigid metallic construction, whereas the rack 503 is of a plastic material. Accordingly, the spring loading of rollers 506 and 507 upwardly against the rack effectively prevents gear backlash. In the event that a different construction is employed, wherein backlash occurs, or in the unlikely event that the gear wear or the like should introduce a backlash factor at the times of reversal of rack 503, an optional backlash correction may be provided at 526, intermediate the counter 518 and the display 521 and 524, and replacing the direct connection 525 as shown in FIG. 5. Since in effect gear backlash tends to insert altered mechanical response into the system, the backlash correction 526 functions to change one or more bits in the encoded representation provided to processor 521 and 524, whereby the unwanted mechanical responses change due to backlash at gears 502 and 505 are compensated by insertion of corresponding, known electronic "errors," in the form of altered counts or bits provided by the backlash correction 526.

Since the stepping motor 504 operates transducer 501 by rotation of gear 505 for a half transducer oscillation cycle in one direction, and then for a half transducer oscillation cycle in the other direction, and since such motor switching occurs by routing oscillator pulses from the motor drive via one of lines 515 and 528 or the other, logic 529 is provided to sense respective end points of the arc of rotation of transducer 501, conveniently by being conditioned to detect logically the encoded representation, from counter 518, corresponding to those end points. When an end point of transducer rotation is determined at 529, a motor reverse signal is coupled via line 532 to the motor drive 514, which then proceeds in conventional fashion to slow and stop the motor from progressing in one direction, and then to reverse and accelerate the motor 504 in the opposite direction. In order properly to control the balance of the system during this slowdown, reversal, and acceleration time, the motor drive unit 514 provides, via line 531, an inhibit signal to counter 518, causing it to maintain the end point count in storage until the stepping motor 504 has been decelerated, reversed, and accelerated in the proper direction. Typically, on a per cycle basis, this switching procedure may occupy the range of ten percent of the time required for a full oscillation cycle of the transducer 501. Accordingly, mechanical imprecision at this point will be the primary deteriminant regarding the necessity to provide backlash correction at 526.

In a preferred embodiment, the system specified in FIG. 5 is adapted to produce an image field of 256 by 256 picture elements. In such an embodiment, the transducer 501 has 256 successive positions between end points. The transducer 501 is adapted to fire a transmit pulse during specified ones of the 256 incremental steps or positions followed by the transducer from one extreme angle to the other.

Accordingly, each such transducer position may be conveniently assigned a different 8 bit binary count, with each such count further representing a vertical line of data in the 256 by 256 picture element display. Generally, from the observer's standpoint, an interleaved pattern of imaging is preferable whereby alternate lines (e.g. those encoded as an odd number) are characterized by a transmit-receive sequence as the transducer nods in one direction (e.g. counterclockwise), whereas alternate inter leaved lines (e.g. those encoded by an even number) are characterized by a transmit-receive sequence during the other half cycle of transducer oscillation. In this fashion, a full 256 by 256 frame of data is produced for each single full oscillation cycle of the tranducer 501.

For purposes of such an interleaved pattern, it will be apparent that only alternate ones of the pulses produced by Hall effect switch 513 are to be employed to reset the counter 518 via reset line 519. Such processing is accomplished by flip flop 533.

In a preferred embodiment, the leftmost position of transducer 501 is assigned the coded value of zero, the rightmost excursion of the transducer 501 is assigned the coded value of 255, and the midpoint, or horizontal transducer position is assigned the coded value of 128. Hence, pulses to the counter 518 via line 517, accompanying clockwise rotation, increment the counter from encoded representations of zero through 255, whereas decrementing pulses via line 527, corresponding to counterclockwise rotation of the transducer 501, decrement the count in the counter backwardly from 255 through zero. Whenever a reset pulse from switch 513 via line 519 is coupled to counter 518 for reset purposes (i.e., in the interleaved display situation, one for every two pulses actually produced by the switch 513), the encoded representation in counter 518 is forced to the value 128, corresponding to the midpoint position.

In an optional approach, an "electronic zoom" effect may be achieved by slight logical alteration from the foregoing preferred mode of operation. This may be based in part upon the fact that although motor 504 and hence also transducer 501, is actually stepping from position to position, the whole process is accomplished quite rapidly, and in fact transducer 501 is in quasi-continuous motion. Accordingly, if multiple pulses are energized by processor 521 via line 522 for each transmit enable pulse received at line 516, the timing between them will be separated by some motion of transducer 501. Hence, twice as many pulses A-scan lines per half oscillation cycle permit, on a lateral scale, twice the magnification or granularity as normally employed. Since the display will still be 256 lines wide, then, such transmission at double the normal rate should occur during but half the arc of traversal of the transmitter 501 but still centered on switch 513. It is clear that such may be achieved by routine alteration of counter 518 to transmit suitable enabling signals to processor 521 via line 516.

In summary, then, in accordance with the principles of the present invention as disclosed herein, the sweep of an oscillating transducer is controlled by the number of steps (or half steps) taken by a motor. An arm, rigidly connected to the transducer shaft, holds a small magnet that passes adjacent to a Hall effect switch, which in turn is rigidly mounted to the housing of the scanner. Each time the transducer "nods," the Hall effect switch gives out a pulse. The parts are oriented in a manner such that the pulse is generated at the center of the swing, or when the transducer is pointing the beam straight up. System counters are reset each time, or alternate times, as desired, the magnet passes the Hall effect device thus insuring that the count end points do not drift physically should a pulse be missed. Each time the number of pulses approaches an end of travel, a deceleration of the pulse rate takes place to decelerate the inertia of the system prior to stopping for turnaround. As the motor stops and then is accelerated in the opposite direction, counts are forestalled until full reverse motion is achieved.

In this fashion, transducer control and monitoring is achieved by detecting the position of the transducer once during each cycle or half cycle of transducer oscillation, and assuming or predicting the position of the transducer based on passage of time since the most recent occurrence of the transducer at the detected position.

It will be apparent that the foregoing has set forth preferred and illustrative embodiments of the principles of the present invention, but that numerous alternatives will occur to those of ordinary skill in the art without departure from the spirit or the scope of the present invention.

What is claimed is:

1. In an ultrasound imaging system, scan and display control apparatus comprising:
   a. ultrasound transducer means adapted physically to oscillate about a predetermined axis;
   b. transducer positioning means for oscillating said transducer, an increment at a time, through a given arc about said axis, said positioning means including a stepping motor system and control means for energizing said motor system at predetermined time increments;
   c. means for sensing select passages of said transducer means through a given, predetermined portion of said arc, and for generating a reference signal pulse at each said sensed passage;
   d. counting means, responsive to said means for energizing and reset by each said reference signal pulse, for maintaining a representation of cumulative increments travelled by said transducer means from said predetermined position; and
   e. means, responsive to said counting means, for conditioning said positioning means to reverse the direction of oscillation of said transducer means about said axis when said counting means achieves select predetermined counts.

2. Apparatus as described in claim 1 wherein said means for counting comprises appendage means attached to and oscillating with said transducer means, and stationary detector means, located at a predetermined point in the arc of travel of said appendage means, for generating said reference signal pulse upon select passage of said appendage means past said detector.

3. Apparatus as described in claim 2 wherein said appendage means carries a magnet thereon, and wherein said detector means includes a Hall effect detector for sensing adjacent presence of said magnet.

4. Apparatus as described in claim 1 and further including imaging control means, responsive to said counting means, for establishing transmit-receive sequences at said transducer, and for assembling an associated image, image components being interrelated with one another by corresponding interrelation of transmit-receive sequences with associated representations in said counter.

5. In an ultrasound pulse-echo imaging system employing a physically oscillating ultrasound transducer and means for incrementally moving said transducer, an improved method of controlling irradiation of tissue by said transducer comprising the steps of:
   a. detecting the position of said transducer intermittently during each oscillation cycle;
   b. predicting intermediate positions of the transducer based on transducer increments which have occurred since most recent occurrence of the transducer at a detected position; and
   c. assembling an image from transducer pulse echoes by interrelating said pulse echoes based on said detected position and said predicted positions.

6. A method as described in claim 5 wherein said predicting step comprises maintaining a count which is incremented in correspondence with oscillating movement of said transducer, and resetting said count upon each said intermittent detections of position.

7. A method as described in claim 6 wherein said detecting step detects passage of said transducer by a given position once for each transducer oscillation full cycle.

8. A method as described in claim 7 wherein said detecting step includes providing a magnet to travel with said transducer, and detecting alignment of fields generated by said manget with a reference point along the route of travel of said magnet.

* * * * *